United States Patent [19]

Allcock et al.

[11] Patent Number: 4,636,387
[45] Date of Patent: Jan. 13, 1987

[54] ANESTHETIC POLYORGANOPHOSPHAZENES

[75] Inventors: Harry R. Allcock; Paul E. Austin; Thomas X. Neenan, all of State College, Pa.

[73] Assignee: Research Corporation, Tucson, Ariz.

[21] Appl. No.: 708,907

[22] Filed: Sep. 21, 1984

Related U.S. Application Data

[62] Division of Ser. No. 390,345, Jun. 21, 1982, Pat. No. 4,495,174.

[51] Int. Cl.$^4$ .................. C08G 79/02; C08G 79/04; A61K 9/58
[52] U.S. Cl. ........................... 514/89; 546/22; 560/46; 560/49; 564/12; 564/13; 514/110; 514/118; 514/124; 424/78
[58] Field of Search ............. 546/22; 560/48, 64, 560/46, 49; 564/12, 13; 424/78; 514/110, 124, 89, 118

[56] References Cited

U.S. PATENT DOCUMENTS 3,914,283 10/1975 Okamoto et al. ............ 560/49
4,495,174 1/1985 Allcock et al. .............. 424/78

OTHER PUBLICATIONS

Allcock et al., Chemical Abstracts, vol. 97, No. 2, Abst. No. 6898-Y (Jul. 12, 1982).
Allcock et al., Chemical Abstracts, vol. 102, No. 20, Abst. No. 172,651d, (May 20, 1985).

*Primary Examiner*—Alan L. Rotman
*Attorney, Agent, or Firm*—Scully, Scott, Murphy & Presser

[57] ABSTRACT

A long-acting, local anesthetic, comprising a polymeric phosphazene backbone, and certain radicals having local anesthetic activity and an amino functional group on the ring of said radical through which said radical is covalently attached to the phosphazene backbone by a phosphorous-nitrogen single bond is disclosed along with medicaments containing such anesthetics. The radicals employed are 2-amino-4-picoline, benoxinate, naepaine and phenacaine.

10 Claims, No Drawings

4,636,387

ANESTHETIC POLYORGANOPHOSPHAZENES

This is a divisional of copending application Ser. No. 390,345, filed on June 21, 1982, now U.S. Pat. No. 4,495,174, issued Jan. 22, 1985.

BACKGROUND OF THE INVENTION

1. Field of the Invention

The present invention relates to a long-acting local anesthetic and more particularly to an anesthetic formed by covalently linking a small molecule having local anesthetic activity to polyphosphazene.

2. Description of the Prior Art

Many useful anesthetics and analgesics, such as codeine and procaine, have been developed for the treatment of persistent localized pain. However, such medicaments are not without their own problems. Systemic anesthetics affect the entire nervous system and are not useful for control of localized pain. Mild analgesics, such as aspirin, may be ineffective against severe pain while stronger analgesics, such as codeine and the related narcotics, produce many undesirable side effects.

One useful class of anesthetics for the treatment of localized pain is the local anesthetics. These are drugs that produce loss of sensation and motor activity in a restricted area of the body by reversibly blocking conduction in nerve fibers. However, such drugs often have undesirable side effects caused by their high concentration in the blood either at the point of injection or systemically. Such high concentration are needed initially since the known local anesthetics are short-lived and are metabolized in plasma or the liver. Even if only a low dose is needed to produce the desired degree of anesthetic, a higher dose must be administered in order to produce an anesthetic effect of suitable duration, since multiple injections traumatize the patient and are undesirable. Accordingly, there exists a need for a local anesthetic in a long-acting, slow-release form.

Various publications have disclosed long-acting medicaments of various types. For example, U.S. Pat. Nos. 3,887,699 to Yolles, 3,983,209 to Schmitt, and 4,130,639 to Shalaby et al have disclosed incorporation of a drug into a biodegradable polyester composition. Water-soluble or biodegradable polyorganophosphazenes have recently come into use in this area. The use of water-soluble polyorganophosphazenes as carriers for coordinatively bonded platinum-containing anti-cancer drugs is disclosed in Allen et al, *J. Am. Chem. Soc.*, 99, 3987 (1977) and Allcock et al, ibid, 3984 (1977). Likewise, U.S. Pat. No. 4,239,755 to Allcock et al discloses a medicament comprising steroidal cyclotriphosphazenes.

The chemistry of polyphosphazene polymers, although not established to the extent known for organic polymers, is becoming better known. A recent review in this area indicative of the known chemistry of these macromolecules is Allcock, "High Polymeric Organophosphazenes," *Contemporary Topics in Polymer Science*, 3, 55 (1979) which is herein incorporated by reference.

However, none of these references disclose or suggest the preparation of a long-acting local anesthetic, and the need for such substances still exists.

SUMMARY OF THE INVENTION

Accordingly, it is an object of this invention to produce a local anesthetic in a long-acting, slow-release form.

It is a further object of this invention to provide a long-acting anesthetic using a small molecule having known anesthetic activity and known toxic side effects but to provide it in a novel slow-release form.

These and other objects of the invention, as will hereinafter become more readily apparent, have been accomplished by providing a long-acting local anesthetic comprising a polymeric phosphazene backbone and an organic radical having local anesthetic activity and an amino or hydroxyl functional group on an aryl ring through which said radical is covalently attached to said phosphazene backbone by a phosphorous-nitrogen or phosphorous-oxygen single bond.

DESCRIPTION OF THE PREFERRED EMBODIMENTS

The present invention arose with the discovery that, when proper controls are used, known local anesthetic agents having typical short lifetimes can be converted, by covalentingly attaching them to the covalent backbone of a polyphosphazene, into molecules which slowly release the small molecules as anesthetics as the polymeric backbone hydrolyzes.

Local anesthetics are drugs that produce loss of sensation and motor activity in a restricted area of the body by reversibly blocking conduction in nerve fibers. The first local anesthetic to be introduced into clinical practice was cocaine in 1884. However, cocaine was soon determined to have undesirable side effects and synthetic analogs were introduced. In order for an anesthetic to be useful as a local anesthetic, it should possess the following properties: effectiveness whether used topically or parenterally; inertness to the tissue to which it is applied except for nerve tissue; rapid onset of anesthesia; low systemic toxicity; stability to heat and storage; and solubility in suitable pharmaceutical carries. No known local anesthetic is ideal. However, many local anesthetics are known and can be used with the present invention. Some of these, identified by their generic names, are the following: 2-amino-4-picoline, benoxinate, benzocaine, bupivacaine, butethamine, butyl-4-amino-benzoate, chloroprocaine, cocaine, cyclomethycaine, dibucaine, dimethisoquin, diperodon, dyclonine, hexylcaine, lidocaine, mepivacaine, meprylcaine, metabutethamine, naepaine, phenacaine, piperocaine, pramoxine, prilocaine, procaine, proparacaine, propoxycaine, pyrrocaine and tetracaine. Preferred local anesthetics are compounds already having an unsubstituted amino group directly attached to an aryl ring because of the ease with which these compounds can be attached to the polyphosphazene backbone. Examples of such compounds include procaine, benzocaine, chloroprocaine, p-aminobenzoic acid butyl ester, and 2-amino-4-picoline.

Previous approaches for prolonging the activity of procaine-like compounds were based on changes in the molecular skeleton of the molecules, such as increasing the size of the amino alkyl group, lengthening the alkalene chain, or introducing alkyl groups into the 4-amino unit. In the present invention, the object is to modify the duration of the biological activity by linking the active molecule to a polyphosphazene skeleton. As will be discussed shortly, there are many known methods of attaching small molecules to the backbone of a polyphosphazene polymer. Compounds containing an amino aryl or hydroxy aryl functional group are preferred because of the ease with which these molecules can be attached to the polyphosphazene backbone.

Since most known local anesthetics have one of these functional groups, or they can be modified synthetically to contain such a group by known reactions of organic chemistry, such compound are useful in the practice of this invention. Preferred are compounds already known to have local anesthetic activity and already having an amino functional group attached to an aryl ring, particularly a phenyl ring. Of these, those compounds in which at least one, and preferably both, of the positions ortho to the amino group are unsubstituted (i.e., contain hydrogen at those positions) are particularly preferred since such molecules are more easily attached to the phosphazene backbone. Examples of some of the preferred local anesthetics are 2-amino-4-picoline, benoxinate, benzocaine, butethamine, butyl 4-aminobenzoate, chloroprocaine, metabutethamine, naepaine, phenaeaine, procaine, proparacaine, propoxycaine, and tetracaine.

If a local anesthetic does not contain an aryl amino group, it may still be used in accordance with this invention if modified to contain a hydroxy aryl or amino aryl group. For example, dyclonine, which is 1-(4-butoxyphenyl)-3-(1-piperidinyl)-1-propanane, contains a "hidden" hydroxy group which can be released by cleavage of the butyl ether with HI to free the hydroxy phenyl group. Other anesthetics, such as piperocaine, which is 2-methyl-1-piperidinepropanol benzoate, which are derivatives of benzoic acid, may be converted into compounds capable of being attached to the phosphazene backbone by synthesizing them from p-aminobenzoic acid rather than benzoic acid. Other synthetic routes to deserved compounds are equally useful and are well within the skill of an organic chemist. Examples of suitable synthetic techniques are found in, for example, Weyhgand et al, Preparative Organic Chemistry, John Wiley & Sons, New York, 1972, which is herein incorporated by reference.

The key to synthesizing the compounds of the present invention lies in the chemistry of the polyphosphazene polymer backbone, which will be briefly reviewed prior to discussing the specific embodiments of the invention. Polyphosphazene polymers possess a highly unusual backbone structure composed of an inorganic chain of alternating phosphorus and nitrogen atoms. Some typical polyorganophosphazene structures are shown in I–IV.

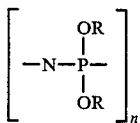
I

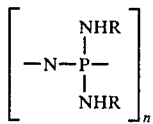
II

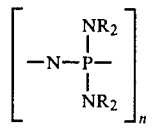
III

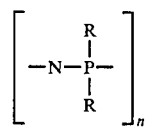
IV

In these macromolecules the group R is an organic residue and n may be from 3 to 30,000.

The most striking difference between conventional polymers and poly(organophosphazenes) is in their method of synthesis. The normal techniques for the synthesis of macromolecules—i.e., the polymerization of unsaturated monomers or the condensation reactions of difunctional monomeric reagents—are not applicable to polyphosphazene synthesis. Monomers of structure, $N\equiv P(OR)_2$, $N\equiv P(NHR)_2$, $N\equiv P(NR_2)_2$, or $N\equiv PR_2$, have not yet been isolated.

The key to the synthesis of poly(organophosphazenes) is the use of a preformed, linear, high polymeric halogenophosphazene as a highly reactive intermediate for substitution reactions. A few organic polymers are prepared by the modification of preformed macromolecules (for instance, the formation of poly(vinyl alcohol) from poly(vinyl acetate), or the chloromethylation of polystyrene), but this method of synthesis cannot be applied generally because of the low reactivity of most organic polymers and the well-known problems that result from chain-coiling in solution or from the deactivation induced by charge generation on nearby repeating units. This modification method, however, forms the main synthetic route to the polyorganophosphazenes.

The overall synthesis routes for poly(organophosphazenes) are shown in Scheme 1.

Scheme 1.
General synthesis routes to poly(organophosphazenes)

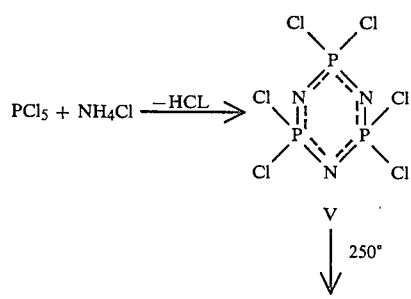

-continued
Scheme 1.
General synthesis routes to poly(organophosphazenes)

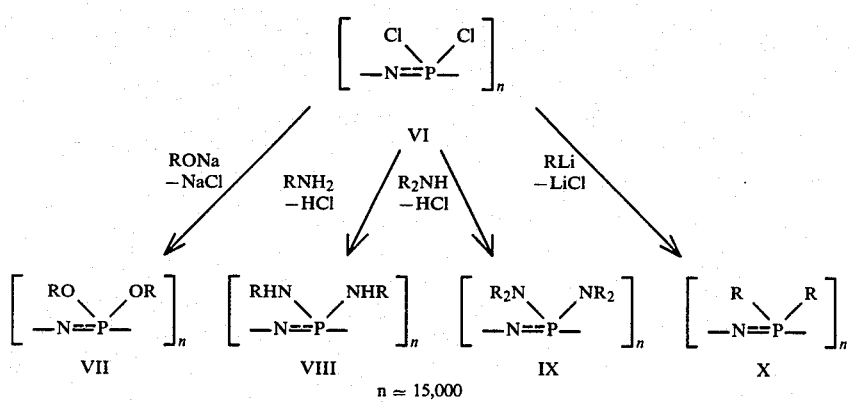

n ≃ 15,000

The formation of hexachlorocyclotriphosphazene (V) from phosphorus pentachloride and ammonium chloride or ammonia has been known since the work of Liebig and Wohler in 1834. Similarly, the thermal polymerization of V to a rubbery, crosslinked form of polydichlorophosphazene (VI) was reported by Stokes as early as 1897. However, for over 70 years this polymer was viewed merely as a laboratory curiosity because it is hydrolytically unstable in the atmosphere and is insoluble in all solvents. However, it has since been shown that the polymerization of V to VI is a two-step reaction. During the initial stages of the polymerization (up to ~70-75% conversion of V to VI) an uncrosslinked form of VI is formed. This polymer is soluble in a number of organic solvents, such as benzene, toluene, or tetrahydrofuran. Beyond this stage, the polymer crosslinks rapidly. The mechanism of this crosslinking process is still not fully understood, although traces of water will accelerate the process, possibly by yielding P-O-P bridging links.

The formation of the uncrosslinked polydichlorophosphazene has been reported in various references and is not considered to be part of the present invention. This synthesis and the synthesis of various polymers therefrom, such as I-IV, have been reported in, for example, Allcock and Kugel, *J. Am. Chem. Soc.*, 87, 4216 (1965); Allcock et al, *Inorg. Chem.*, 5, 1709 (1966); and Allcock and Kugel, *Inorg. Chem.*, 5, 1716 (1966), all of which are herein incorporated by reference.

In solution, the uncrosslinked form of VI is a highly reactive species. It reacts rapidly with alkoxides, amines, and some organometallic reagents to yield polymers, such as I-IV.

Investigators in the laboratories of the present inventors have recently developed a modification to this general synthesis route, specifically for the purpose of preparing polymers of structure, II. Polydichlorophosphazene (VI) reacts with organometallic species such as Grignard or organolithium reagents by two different reaction pathways—one favorable and one distinctly unfavorable. These two reactions are alkylation or arylation (XII) on the one hand, and chaincleavage (XIII) on the other.

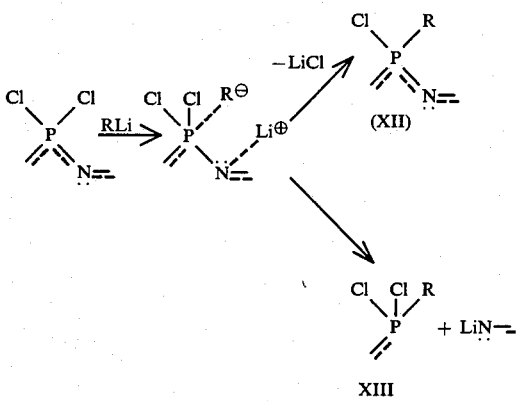

Because the chain cleavage reaction is presumably favored by a high electron-density in the lone-pair-electron orbital at skeletal nitrogen, the inventors have used the more electronegative fluorine atoms in poly(difluorophosphazene) to favor halogen substitution at the expense of chain cleavage. Poly(difluorophosphazene) (XV) can be prepared by the high pressure, high temperature polymerization of hexafluorocyclotriphosphazene (XIV). Once again this is a two-step process. In the first step the reaction mixture contains only a decreasing amount of XIV and an increasing proportion of uncrosslinked XV. In the second stage, XV crosslinks, often when the conversion of XIV to polymer has arisen above ~70%. The reactions of XV with organometallic reagents yield alkylated or arylated high molecular weight polymers, although 100% alkylation or arylation has not yet been achieved without appreciable chain cleavage.

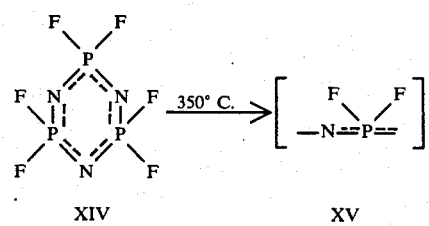

In polyphosphazene chemistry an enormous range of different polymers can be prepared by relatively simple techniques from one or two preformed polymeric starting materials. This means that the polymerization problem is a relatively trivial aspect of the synthesis. Different polymers are prepared from the same starting materials merely by modifying the side groups.

This unusual synthetic versatility can, in principle, give rise to an almost unprecedented range of new macromolecules. However, it is important to note that certain restrictions exist with respect to the types and combinations of different substituent groups that can be attached to the polyphosphazene chain.

First, the nucleophilic substitution reactions of poly(dihalophosphazenes) generally fall into the category of $S_N2$-type replacements. Hence, they are affected by the nucleophilicity and steric characteristics of the attacking nucleophile and and by the leaving-group ability of the halogen. Second, restrictions exist when a prospective nucleophile possesses two or more potential nucleophilic sites. For example, a difunctional reagent (a diamine or diol) could crosslink the chains. Third, as mentioned previously, the possibility exists that the cleavage of phosphorus-nitrogen skeletal bonds might become competitive with phosphorus-halogen bond cleavage. A few examples will illustrate some of the specific restrictions that have been identified.

The reactions of amines with poly(dihalophosphazenes) are, in general, more sensitive to mechanistic restrictions than are the substitutions by alkoxides or aryloxides. For example, diethylamine replaces only one chlorine per phosphorus in VI to yield polymers of structure, XVI.

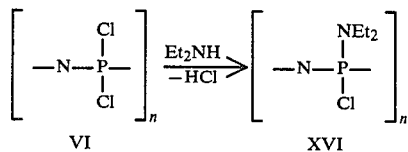

Diphenylamine apparently undergoes no substitution at all. These results reflect the sensitivity of the aminolysis reaction to steric effects and to the nucleophilicity of the amine. Moreover, if poly(difluorophosphazene) (XV) is used as a polymeric intermediate, even primary amines replace only one fluorine per phosphorus, under conditions whre total halogen replacement occurs with polydichlorophosphazene. This effect is ascribed partly to the poor leaving-group ability of fluorine compared to chlorine. Steric effects are particularly

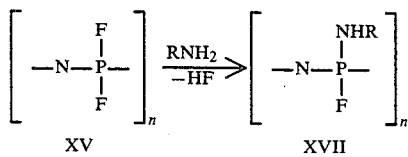

noticeable when bulky nucleophiles such as the steroidal anion shown in XIX are employed. Only one of these molecules can be introduced every three or four repeating units along the polymer chain, and some difficulty is encountered when attempts are made to replace the remaining halogen atoms by less hindered nucleophiles.

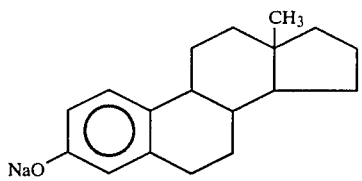

The crosslinking reactions by difunctional reagents are facile processes. Aliphatic or aromatic diamines or the alkoxides generated from diols readily crosslink the chains, either by halogen replacement or, in some cases, by the displacement of organic groups already present. Even ammonia or methylamine can function as crosslinkage agents. However, methylamine does not crosslink the chains at low temperatures, and ethylamine and higher alkyl or primary amines function exclusively as mono- rather than di-nucleophiles.

Perhaps the most serious restriction to the diversification of polyphosphazene structures is found in the tendency of many reagents to induce chain cleavage. The role of organometallic reagents in chain cleavage has already been mentioned. However, carboxylic acids and their alkali metal salts are particularly effective chain-cleavage agents. The mechanisms of these cleavage reactions are only partly understood. Nevertheless, this reaction pathway precludes the use of many biologically active agents as substituent groups unless special care is taken in attaching such radicals to the backbone.

The chemical characteristics of poly(organophosphazenes) can be understood in terms of two factors—the nature of the backbone and the structure of the side group. The chemistry of the backbone is dominated by the presence of the lone-pair electrons on the skeletal nitrogen atoms. The basicity of these nitrogen atoms facilitates protonation, coordination to metals, or hydrogen bonding to water or other protice solvents. For example, the polymer $[NP(NHCH_3)_2]_n$ forms acid-base "salts" with hydrohalides, functions as a polymeric ligand for transition metals such as platinum, and at the same is soluble in water or alcohols.

An equally powerful influence on the chemical properties is exerted by the side group structure—sometimes in opposition to the skeletal influence. For example, although the $CH_3NH$- side group confers water-solubility on the polymer, fluorinated side groups, such as $CF_3CH_2O$— or $CF_3CF_2CH_2O$—, give rise to hydrophobicity and water-insolubility. However, these latter side groups provide solubility in ketones or fluorocarbons. The phenoxy group imparts solubility in hot, aromatic hydrocarbons, but insolubility in nearly all other media. Thus the hydrophobicity or hydrophilicity of a polymer can be varied over a wide range by a choice of suitable side groups.

The hydrolytic stability of a polyphosphazene is markedly dependent on the type of side group. Nearly all poly(organophosphazenes) are stable to aqueous media, but the most hydrophobic species are remarkably resistant to hydrolytic degradation. The polymers $[NP(OCH_2CF_3)_2]_n$ and $[NP(OC_6H_5)_2]_n$, are unaffected after years of immersion in strong aqueous sodium hydroxide solution. However, a limited number of side groups are hydrolytic destabilizing groups. For example, polymers that possess $-NH_2$ or $-NHCH_2COOR$ groups hydrolyze slowly with moisture.

Polymers according to the present invention may be synthesized as cyclic trimers using hexachlorocyclotriphosazene, (NPCl$_2$)$_3$, as the starting material, or as linear polymers using polydichlorophophazene, (NPCl$_2$)$_n$, as the starting material. The exact synthetic method will vary with the structure of the polymer being synthesized but will typically consist of two basic steps: reaction of the intermediate polyhalophosphazene with the molecule having anesthetic activity either preceeding or followed by replacement of the remaining halogens with the inactive side groups.

Polymers may be synthesized containing only active side groups if desired, but it is preferred to synthesize mixed polymers for ease of control of the physical properties of the polymers. Inactive side groups can be used to impart water solubility, water insolubility, or biodegradability as was previously discussed. When mixed polymers are synthesized, it is preferred to form the inactive side groups first since these generally contain fewer functional groups that may interfer with later reactions. This is essential if alkyl or aryl groups are attached directly to the phosphorous of the backbone because of the reactive organometallic reagents used to carry out this reaction. In general there are few limitations on the types of functional groups present in possible inactive side groups; the only prohibited functional groups are those in which a hydrogen is attached to a nitrogen, oxygen, or sulfur. Such functional groups can cause crosslinks to form with other polymer chains or cause undesirable chain cleavage. Examples of undesirable functional groups are hydroxyl, carboxylic acid, primary and secondary amino thiol, and sulfonic acid groups. However, —NH$_2$ attached to the phosphorous of the backbone is acceptable. Preferred precursors of inactive side groups have the formula HQJ where Q represents —NR— (R is hydrogen or methyl), —O—, or a covalent bond and J represents

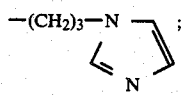

L, where L represents H, a C$_1$-C$_{12}$ alkyl group, or a C$_2$-C$_{12}$ alkyl group substituted by a halogen atoms or —CN or interrupted by a divalent organic functional group of the formula —O—, —COO—, —CONR$^1$, —R$^1$C=CR$^1$—, —C≡C—,

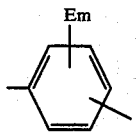

or —CO—, where each R$^1$ independently represents hydrogen or a C$_1$-C$_4$ alkyl group, m is an integer from 0 to 4, and each E independently represents a halogen atom, —NO$_2$, —CN, or R$^1$; or M, where M represents an aryl radical of the formula

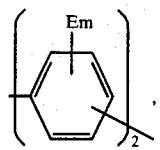

where n is 1 or 2, or

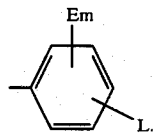

The substituents or divalent oraganic functional groups listed for the C$_1$-C$_{12}$ alkyl groups may independently appear more than once or more than one such substituent or group may be present.

Preferred inactive side groups have —NH— or —O— for Q and only halogen atoms or one of two divalent functional groups present in the remainder of the alkyl or aryl side group. Most preferred inactive side groups are —N(CH$_3$)$_2$, $$-\text{NHCHCO}_2 R^1$$
$$\quad\quad |$$
$$\quad\quad R^2$$

where R$^2$ is the side chain of a naturally occuring amino acid,

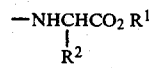

—OCH$_2$CF$_3$ and other fluorinated C$_2$-C$_4$ alkoxy groups,

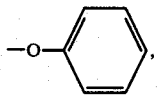

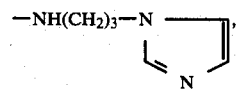

and —NH$_2$.

Replacement of chlorine atoms in the backbone of the polyhalophosphazene is carried out in an aprotic organic solvent, preferably an aromatic hydrocarbon such as toluene, by reacting the side group percurser HQJ; its salt GQJ, where G is an alkali metal ion; or the organometallic reagent UJ (where Q is a covert bond), where U is a metal ion with the polyhalophosphazene. The ratio of inactive to active side groups is easily controlled by controlling the mole ratio of percursor HQJ to replaceable chlorine atoms. Suitable ratios include from 100:1 to 1:10. Preferred are ratios of 10:1 to 1:2 with about 3:1 being most preferred.

A trialkylamine may be used as a catalyst when the reaction is carried out with HQJ. Triethylamine is preferred. This reaction is preferred when Q is NH. When Q is O, a reaction with GQJ is preferred.

The polyorganohalophazene intermediate is generally not isolated but is reacted with the small molecule having local anesthetic activity that is to be attached to the polymer backbone. Since this molecule will have either the functional group H₂N—Ar or HO—AR, where Ar is the aryl ring, the reaction is carried out as described above for HQJ and GQJ.

As has been previously discussed, it is preferred that the small molecule having local anesthetic activity be one of the known local anesthetics. However, useful long acting local anesthetics can also be prepared from related compounds of slightly different structure having an aryl ring and one or more side groups (functional group) selected (respectively) from aryl rings and side groups attached to an aryl ring of 2-amino-4-picoline, benoxinate, benzocaine, bupivacaine, butethamine, butyl-4-amino-benzoate, chloroprocaine, cocaine, cyclomethycaine, dibucaine, dimethisoquin, diperodon, dyclonine, hexylcaine, lidocaine, mepivacaine, mepryl- caine, metabutethamine, naepaine, phenacaine, piperocaine, pramoxine, prilocaine, procaine, proparacaine, propoxycaine, and tetracaine or any side chain or aryl group in a molecule known to have local anesthetic activity, for example as listed in The Merk Index, 9th Edition, Merk & Co., Rahway, N.J., 1981, which is herein incorporated by reference.

The resulting polymer may have local anesthetic activity in the polymeric form because of interactions of the active side groups with nerve tissue. It is also possible to design a polymer which will hydrolyze when contacted with water so that the small active molecules are released by chosing inactive side groups that impart hydrolytic instability to the polymer, as has been previously discussed. Likewise, the polymers may be designed to be either soluble or insoluble in water by correctly chosing the inactive side groups.

Insoluble polymers could be surgically implanted, for example in oral surgery. Soluble polymers would be injectable and would diffuse more slowly than the currently available small molecules, thereby prolonging the anesthetic activity by preventing metabolism of the small molecules in the liver. Biodegradable polymers can also be produced and could be used in sutures and the like. Biodegradable (i.e., hydrolizable) phosphazenes are discussed in detail in Allcock et al, *Inorg. Chem.*, 21, 515 (1982), which is herein incorporated by reference.

Polymers of this invention have been demonstrated to release an active local anesthetic by hydrolysis in an aqueous medium. Once hydrolysis begins, the polymer backbone also hydrolyzes to urea and phosphate. The remaining hydrolysis products depend on the nature of the remaining side groups, and may be an amine, amino acid, steroid, alcohol, or other molecule as previously described as suitable side groups. It is possible to release a second active component in this manner so that two beneficial effects simultaneously take place, for example by providing a medicament for a joint injury which releases both a steroid and a local anesthetic.

The compounds of this invention can be employed in mixture with conventional excipients, i.e. pharmaceutically acceptable organic or inorganic carrier substances suitable for topical or parenteral application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous parafin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring and/or aromatic substances and the like which do not deleteriously react with the active compounds.

For parenteral application, particularly suitable are solutions, preferably oil or aqueous solutions, as well as suspension, emulsions, or implants, including suppositories. Ampoules are convenient unit dosages. Solutions, suspensions, and emulsions are also suitable for topical application. Injections, particularly intramuscular injections, are preferred for parenteral application.

Generally, the compounds of this invention are dispensed in unit dosage form comprising 10-500 mg of a pharmaceutical carrier per unit dosage and the amount of active agent of the invention per unit dosage is about 1 to 50 mg. Dosage rated for known local anesthetics may be followed, for example, as disclosed in the 35th Edition of the Physician's Desk Reference (1981), which is herein incorporated by reference.

It will be appreciated that the actual preferred amounts of active compounds being utilized, the particular compositions formulated, the mode of application, and the particular situs and organism being treated. Optimal application rates for a given set of conditions can be ascertained by those skilled in the art using conventional dosage determination tests in view of the above guidelines.

Methods of administering any of the long-acting, local anesthetics disclosed in this application to a human or animal, particularly a domesticated animal, by any of the means and methods disclosed above in order to produce anesthesia are also considered to be part of the present invention.

Having now generally described this invention, the same will be better understood by reference to certain specific examples, which are included herein for purposes of illustration only and are not intended to be limiting of the invention or any embodiment thereof, unless so specified.

EXAMPLE 1

The following procedures were used for the reaction of (NPCl₂)₃ with procaine, benzocaine, chloroprocaine, p-aminobenzoic acid butyl ester, and 2-amino-4-picoline. A schematic diagram of these reactions, along with reactions for Examples 2 and 3, is shown in Scheme 2, which appears after Example 3. Hexachlorocyclotriphosphazene (9) (m.p. 110°–112° C.) was obtained from a trimer-tetramer mixture (Ethyl Corp.) after two vacuum sublimitations at 60° C./0.5 Torr, two recrystallizations from heptane, and two additional vacuum sublimations.

Hexachlorocyclotriphosphazene (2 g., $5.83 \times 10^{-3}$ mol) was dissolved in dry toluene (100 mL). To this was added dropwide a solution of the free amine (4 equiv. for each chlorine atom) in dry THF (100 mL), and excess freshly distilled triethylamine. The solution was heated slowly to reflux, and heating was continued for 96 h. A white precipitate of triethylamine hydrochloride formed slowly. The progress of each reaction was monitored by ³¹P NMR spectroscopy, with completion of the substitution being indicated by the appearance of a singlet in the 0–4 ppm region. The reaction mixture was then cooled, filtered, and solvent was removed from the filtrate at reduced pressure to leave a yellow oil. Methylene chloride was added and the solution was then extracted twice with water, and was dried with anhydrous magnesium sulfate. The organic layer was then added slowly to n-hexane to bring abuot precipitation of an adhesive yellow solid. Tritration with hot n-hexane (to remove residual free base) followed by column chromatography of the residue through silica gel (or neutral alumina) ($CH_2/Cl_2$/ethylacetate eluent) yielded the hexaaminocyclotriphosphazenes as off-white needles (30-70% yields).

The synthesis of the chloroprocaine derivative differed from the procedure described above because the amine was received as its hydrochloride salt. This was treated first with an excess of triethylamine in boiling THF, and the solution was then filtered through a glass coarse fritted funnel into the solution fo the cyclotriphosphazene. The reaction of 2-amino-4-picoline with $(NPCl_2)_3$ required only 48 h at the solvent reflux temperature. In all of these reactions, the co-solvent ratios were not critical, but a 1:1 ratio of toluene to THF gave the best results. Melting points and other characterization data are listed in Table I.

Proton decoupled $^{31}P$ NMR spectra were obtained in dioxane at 40 Mc with the use of a JEOL-PS 100 FT spectrometer equipped with a Nicolet 1080 data processing system and were interpreted as $A_3$ spin systems. Ultraviolet spectra were obtained with the use of a Hewlett Packard 8450 A spectrometer. Infrared spectra of samples as KBr discs or thin films on NaCl plates were obtained using a Perkin Elmer 580 spectrometer. Approximate polymer molecular weight estimations were made with the use a Waters Associates ALC-201 gel permeation chromatography instrument fitted with a 122 cm×1 cm $10^5$ Styragel column for use with THF solvent at a flow rate of 2.4 ml/min. Approximate calibration of the columns was accomplished by means of narrow molecular weight distribution polystyrene standards obtained from Waters Associates. Glass transition temperatures were measured with the use of a Perkins Elmer OSC 20 instrument. These instruments were used in all experimental work unless otherwise noted.

cal shifts were similar when the side group residues were derived from 4-8, presumably because of the separation between the variable units and the skeletal phosphorus atoms. However, these $^{31}P$ chemical shifts (2.9-3.8 ppm) were quite different from those for $(NPCl_2)_3$ (+19 ppm). The $^1H$ NMR spectra were complicated, but the integrated ratios of aliphatic to aromatic protons were consistent with residues derived from 4-8.

Infrared spectra showed evidence for the survival of the phosphazene ring in 10, with characteristic maxima in the 1150-1200 $cm^{-1}$ region. Aromatic C-H bonds were detected from peaks in the 3000-3100 $cm^{-1}$ region, the amino N-H groups were evident from peaks at 3500-3200 $cm^{-1}$, while P-N or C-N stretching modes were detected in the 925-960 $cm^{-1}$ region.

EXAMPLE 2

The following procedures were used for the reaction of high polymeric $(NPCl_2)_n$ with procaine, benzocaine, chloroprocaine, p-aminobenzoic acid butyl esters, and 2-amino-4-picoline. Polydichlorophosphazene (11) was prepared by the thermal polymerization of $(NPCl_2)_3$ at 250° C. for an 8-24 h period in a sealed Pyrex tube (20×2.5 cm). Typically, less than 25% conversion to the high polymer was attempted, and the unreacted trimer was then recovered by sublimation at 60° C./0.5 Torr during 12-24 h. The polymer was soluble in orgfanic media such as toluene or tetrahydrofuran.

Polydichlorophosphazene (15 g, 0.13 mol) was dissolved in toluene (900 mL) to yield a clear, viscous solution. Excess triethylamine was distilled directly into this reaction mixture. A solution of the free base amine (3 equiv. per chlorine atom) in dry THF (400 mL) was added dropwise to the cooled polymer solution. The solution was then heated slowly to reflux, and heating was continued for 168 h, with moisture being rigorously excluded throughout this time period. Evidence that the reaction was complete was obtained from the appear-

TABLE I

Characterization Data for Cyclotriphosphazenes

| Compounds 10 | | Microanalysis | | | UV $\lambda_{max}$ | Infrared C=O band $cm^{-1}$ | m.p. °C. | $^{31}P$ NMR$^a$ PPM | Yield % |
|---|---|---|---|---|---|---|---|---|---|
| | | C | H | N | | | | | |
| where $RNH_2$ = 4 | Calc. | 60.58 | 5.37 | 15.59 | 294 | 1705 | 149-151 | 2.87 | 33 |
| | Found | 60.78 | 5.70 | 15.70 | | | | | |
| 5 | Calc. | 57.90 | 5.36 | 11.26 | 240 | 1675 | 198-200 | 2.94 | 35 |
| | Found | 57.48 | 5.35 | 11.39 | | | | | |
| 6 | Calc. | 53.42 | 6.16 | 11.98 | 310 | 1708 | 144-146 | 3.78 | 72 |
| | Found | 53.39 | 6.33 | 10.37 | | | | | |
| 7 | Calc. | 61.53 | 6.52 | 9.79 | 250 | 1705 | 204 | 3.12 | 68 |
| | Found | 61.56 | 7.53 | 10.14 | | | | | |
| 8 | Calc. | 55.59 | 5.40 | 27.02 | 255 | — | 138 | 3.45 | 42 |
| | Found | 54.57 | 5.50 | 27.51 | | | | | |

$^a$Chemical shift positions were relative to aqueous 85% $H_3PO_4$, where positive chemical shifts represent deshielding. A $D_2O$ capillary lock was used.

All chlorine atoms were replaced in the ultimate products. However, forcing reaction conditions were needed before complete replacement of the chlorine atoms could be accomplished. The products were crystalline materials that were soluble in tetrahydrofuran, methylene chloride, or toluene, but insoluble in water. No residual P-Cl bonds were detected by $^{31}P$ NMR analysis.

The substituted trimers were characterized by a combination of $^{31}P$ NMR, $^1H$ NMR, infrared and ultraviolet spectroscopy, and elemental analysis (see Table I and the Experimental section). The $^{31}P$ NMR spectra were singlets, indicative of hexa-substitution. The $^{31}P$ chemiance of a singlet at 0-7 ppm in the $^{31}p$ NMR spectrum. The reaction mixture was then cooled to 25° C., filtered to remove hydrochloride salts and, on some occasions, the polymer. The clear, yellow filtrate was concentrated in a rotary evaporator. The polymer was isolated by precipitation of the concentrate into n-hexane or by washing the filter cake with water. Two reprecipitations from dioxane into pentane, followed by through Soxhlet extraction with n-pentane, yielded the polymers as pale yellow, film-forming materials. For elemental analysis, the polymer was reprecipitated one more time from dioxane into pentane.

Again, the procedures used for the reaction with chloroprocaine were slightly different. The hydrochloride salt of chloroprocaine was first treated with triethylamine in boiling THF. The mixture was then filtered through a coarse, fritted funnel, under strictly anhydrous conditions, into the solution of poly(dichlorophsphazene). The characterization data are listed in Table II.

tween 1320 and 1100 cm$^{-1}$ plus carbonyl bands in the 1675–1708 cm$^{-1}$ region.

The GPC average molecular weights were in the range of $4 \times 10^5$ to $5 \times 10^5$ values that are somwhat lower than those normally found for poly(arylaminophosphazenes). This may reflect a tendency for depolymeriztion as a consequence of the forcing reaction conditions needed for complete halogen replacement.

Glass transition temperatures are listed in Table II. They are in the range of 27° C. to 58° C., and can be

TABLE II

Characterization Data for High Polymers

| Compounds 11 | | Microanalysis$^a$ | | | $^{31}$P NMR$^{b,c}$ PPM | MW (gpc)$^d$ | Tg (°C.)$^e$ |
|---|---|---|---|---|---|---|---|
| | | C | H | N | | | |
| where RNH$_2$ = 4 | Calc. | 60.58 | 5.37 | 15.59 | 2.5 | 4–5 × 10$^5$ | 50 |
| | Found | 60.48 | 5.70 | 15.70 | | | |
| 5 | Calc. | 57.90 | 5.36 | 11.26 | 6.8 | 4–5 × 10$^5$ | 47 |
| | Found | 56.80 | 5.02 | 11.39 | | | |
| 6 | Calc. | 53.42 | 6.16 | 11.98 | 4.7 | 4–5 × 10$^5$ | 55 |
| | Found | 53.63 | 6.31 | 10.22 | | | |
| 7 | Calc. | 61.53 | 6.52 | 9.79 | 2.7 | 4–5 × 10$^5$ | 48 |
| | Found | 61.62 | 7.46 | 10.06 | | | |
| 8 | Calc. | 55.59 | 5.40 | 27.02 | 0.7 | 4–5 × 10$^5$ | 27 |
| | Found | 53.29 | 5.32 | 26.89 | | | |

| Compounds 14 | | Microanalysis | | $^{31}$P NMR (PPM)$^f$ | MW (gpc)$^d$ | Tg (°C.)$^e$ | Substituent$^{g,h}$ Ratio: x:y:z |
|---|---|---|---|---|---|---|---|
| | | C | H | | | | |
| where RNH$_2$ = 4 | Calc. | 55.19 | 7.62 | (8, 5, 2.5) | 5 × 10$^5$ | 58 | 1:1:1 |
| | Found | 54.70 | 7.41 | | | | |
| 8 | Calc. | 44.20 | 7.20 | (8, 6, 0.7) | 5 × 10$^5$ | 44 | 1:1:1 |
| | Found | 43.49 | 9.62 | | | | |

Notes
$^a$Analytical data were obtained by Galbraith Laboratories.
$^b$All samples were proton decoupled and were interpreted as A$_n$ spin systems for the homopolymers.
$^c$Chemical shift positions were relative to aqueous 85% H$_3$PO$_4$. A D$_2$O capillary lock was used.
$^d$The range of values shown represent gel permeation chromatography results from different synthesis reactions.
$^e$By differential scanning calorimetry.
$^f$Three broad singlets were observed in the $^{31}$P NMR due to the three different phosphorus environments corresponding to NP(NHCH$_3$)$_2$; NP(NHCH$_3$)(NHR); NP(NHR)$_2$. Each peak was well resolved. The peaks were of equal intensity and equal area integration. Thus, the cosubstituent ratio was assumed to be 1:1:1.
$^g$Substituent ratio and composition of the polymers was determined by graphical and computer-based fits to the analytical data.
$^h$Residual chlorine of <1% in all polymers was attributed to bound HCl, with the exception of the chloroprocaine derivatives. Evidence of this view was obtained from a correlation of the microanalysis, $^{31}$P NMR data, and the decrease inthe chlorine content following treatment with triethylamine.

Preliminary experiments indicate the the procaino-substituted high polymers undergo a slow hydrolysis in buffered aqueous media at pH 7. No evidence was found for crosslinking during the high polymer reactions, at least under the dilute reaction conditions employed. Thus, it seems clear that arylamines of this type are not subject to the crosslinking side reactions that can occur with the lower primary alkyl amines. Presumably this reflects a greater steric shielding by the aryl reagents. All the polymers were soluble in organic solvents. Only the mixed substitutent polymer (14) was appreciably soluble in neutral aqueous media. Evidence for polyelectrolyte behavior was found when the polymers were dissolved in aqueous acid. As shown in Table II, the elemental microanalyses corresponded to structures 12–14. (The ratios of the different substituent groups in 14, deduced by microanalysis, are shown in Table II).

$^{31}$P NMR spectra of the homopolymers, 12, showed a sharp singlet only, with chemical shifts at 2.5 (procaino derivative), 6.8 (benzocaino), 0.7 (picolino), 2.7 (p-aminobenzoic acid butyl ester), and 2.5 ppm (chloroprocaino). The spectra of the mixed substituent polymers, 14, were remarkably simple. They showed three equivalent $^{31}$P NMR peaks that were compatible with the presence of equal concentrations of P(NHCH$_3$)$_2$, P(NHCH$_3$) (NHR), and P(NHR)$_2$ units.

The infrared spectra for all the polymers showed characteristic —P=N— "stretching" absorptions becompared to the value of 91° C. for [NP-(NHC$_6$H$_5$)$_2$]$_n$. Hydrogen bonding undoubtedly plays a part in reducing the torsional mobility of polyphosphazenes of this type, compared to, say, [NP(OC$_6$H$_5$)$_2$]$_n$ (Tg= −8° C.).

EXAMPLE 3

Mixed substituent polymers containing methylamino/procaino and methylamino/2-amino-4-picolino side groups were synthesized to produce polymers having high solubility in aqueous media. Polydichlorophosphazene (29 g, 0.25 mol) was dissolved in dry toluene (1500 mL) under strictly anhydrous conditions, in a 3L, 3-necked flask equipped with an overhead stirrer, dry ice condenser, and nitrogen inlet. Triethylamine (70 mL) was distilled directly into this solution, followed by methylamine (16.6 ml, 0.375 mol), previously condensed at −78° C. over sodium spheres. During these additions the temperature of the reaction mixture was maintained at 0° C. The mixture was stirred for 2 h. during which time a copious precipitate of triethylamine hydrochloride was formed.

The solution was then divided equally into two 3-necked, 3L flasks, each equipped with condenser, nitrogen inlet, and mechanical stirrer. To one flask was added procaine (free base) (82.3 g, 0.35 mol) in THF (500 mL). The temperature of the reaction mixture was maintained at 2° C. or lower during the addition. The mixture was then stirred at 0° C. for 24 h, was allowed to warm to 25° C., and was stirred at this temperature for 180 h. $^{31}P$ NMR spectroscopy at this point showed three distinct sets of resonances, none of which could be ascribed to P-Cl units. The reaction mixture was filtered and the filtrate concentrated under reduced pressure to a volume of 300 mL. The concentrate was added to hexane to precipitate the polymer as an off-white powder. This was Soxhlet extracted with hexane and was precipitated twice from THF or dioxane into n-pentane.

The second half of the initial reaction mixture was treated with 2-amino-4-picoline (35 g, 0.324 mol) in dry THF (500 mL). The subsequent steps were similar to those described above. The product was a white powder.

The methylamino side groups were introduced into the mixed substituent system first in order to avoid a possible reaction of the ester function of 4-7 with free methylamine. Mild reaction conditions (−50° to +25° C. in a THF/methylamine co-solvent system at 760 Torr) allowed roughly 50% of the chlorine atoms in 11 to be replaced by methylamino groups to yield 13. Essentially all of the remaining chlorine atoms in 13 could then be replaced by treatment with procaine (4) or 2-amino-4-picoline with the use of the more vigorous reaction conditions (40° C.) established earlier for the homopolymers. However, these conditions must not be so forcing that the methylamino side groups already present can generate crosslinks by reaction with P-Cl groups still present. After completion of the reactions, no residual P-Cl bonds were detected by $^{31}P$ NMR analysis. The trace amounts of residual chlorine (<1%) that were detected by elemental microanalysis were attributed to small amounts of hydrogen chloride bound as a salt to the skeletal or side group nitrogen atoms. No evidence was found that the cosubstitution reaction was accompanied by displacement of methylamino groups already present.

Scheme II

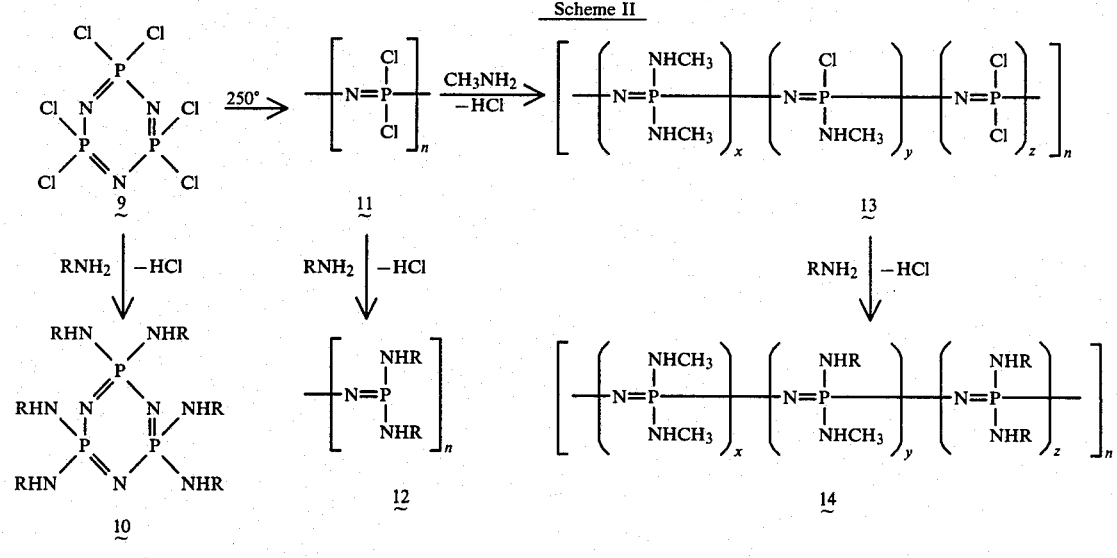

Where $RNH_2$ = 4 - 8

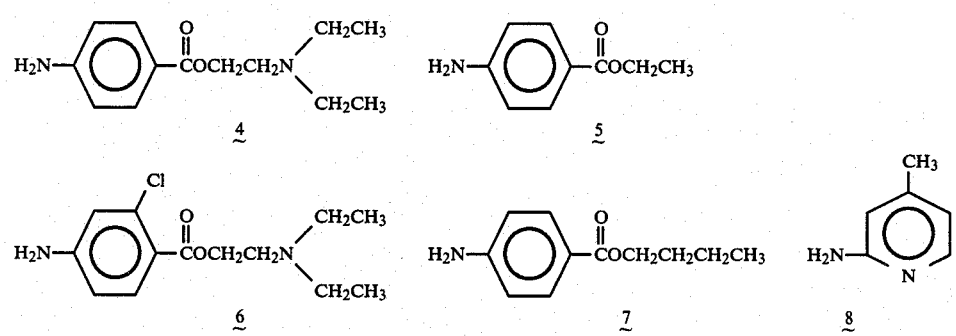

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A long-acting, local anesthetic, consisting of a polymeric phosphazene backbone, and an organic radical having local anesthetic activity and an amino functional group on the ring of said radical through which said radical is covalently attached to said phosphazene backgone by a phosphorous-nitrogen signal bond, said organic radical being selected from the group consisting of 2-amino-3-picoline, benoxinate, naepaine and phenacaine.

2. The local anesthetic of claim 1, wherein said polymeric phosphazene backbone is a cyclic trimer.

3. The local anesthetic of claim 1, wherein said polymeric phosphazene backbone is a linear chain containing from 3 to 30,000

repeating units.

4. The local anesthetic of claim 3, wherein said backbone contains from 100 to 20,000 repeating units.

5. The local anesthetic of claim 3, wherein said backbone contains about 15,000 repeating units.

6. A long-acting local anesthetic medicament, comprising a local anesthetic effective amount of a compound of claim 1 in admixture with a pharmaceutically acceptable carrier.

7. The local anesthetic of claim 1 wherein said organic radical is a radical of 2-amino-4-picoline.

8. The local anesthetic of claim 1 wherein said organic radical is a radical of benoxinate.

9. The local anesthetic of claim 1 wherein said organic radical is a radical of naepaine.

10. The local anesthetic of claim 1 wherein said organic radical is a radical of phenacaine.

* * * * *

UNITED STATES PATENT AND TRADEMARK OFFICE
CERTIFICATE OF CORRECTION

PATENT NO. : 4,636,387

DATED : January 13, 1987

INVENTOR(S) : Harry R. Allcock et al.

It is certified that error appears in the above-identified patent and that said Letters Patent are hereby corrected as shown below:

IN THE SPECIFICATION

Column 2, line 20: "covalentingly" should read --covalently--

Columns 3, 4 & 7: in structures I to IV, VI, XVI, XV and XVII, the valences for the nitrogen and phosphorous atoms should read $$-\!-\!\underset{|}{\overset{|}{N}}\!-\!\underset{|}{\overset{|}{P}}\!-\!-$$

Column 9, line 23: "interfer" should read --interfere--

Column 10, line 5: the subscript "2" should read --n--

Column 12, line 23: "the" should read --and the--

Column 12, line 24: "and the" should read --will depend on the--

Column 12, line 56: "dropwide" should read --dropwise--

Column 13, line 2: "abuot" should read --about--

Column 13, line 14: "fo" should read --of--

UNITED STATES PATENT AND TRADEMARK OFFICE
CERTIFICATE OF CORRECTION

PATENT NO. : 4,636,387

DATED : January 13, 1987

INVENTOR(S) : Harry R. Allcock et al.

It is certified that error appears in the above-identified patent and that said Letters Patent is hereby corrected as shown below:

IN THE CLAIMS

Claim 1, column 18, line 60: "backgone" should read --backbone--.

Signed and Sealed this

Twenty-ninth Day of December, 1987

Attest:

DONALD J. QUIGG

Attesting Officer

Commissioner of Patents and Trademarks